United States Patent [19]

Williams et al.

[11] Plant 4,499

[45] Feb. 5, 1980

[54] DISTINCT CULTIVAR OF APPLE TREE: COOP 16

[75] Inventors: Edwin B. Williams, Lafayette; Jules Janick; Frank H. Emerson, both of West Lafayette, all of Ind.; Daniel F. Dayton, Urbana, Ill.; L. Fredric Hough, Bloomsbury; Catherine H. Bailey, Englishtown, both of N.J.

[73] Assignee: Purdue Research Foundation, West Lafayette, Ind.

[21] Appl. No.: 964,578

[22] Filed: Nov. 6, 1978

[51] Int. Cl.[2] ..... A01H 5/03

[52] U.S. Cl. ..... Plt./34

[58] Field of Search ..... Plt./34

*Primary Examiner*—Robert E. Bagwill

*Attorney, Agent, or Firm*—John R. Nesbitt

[57] ABSTRACT

A new and distinct cultivar of apple tree which is distinctly characterized by its high fruit quality, its resistance to infection caused by *Venturia inaequalis* (Cke.) Wint., the casual agent for the apple scab disease, due to the fact that this new cultivar carries the genetic factor $V_f$, and closely resembles 'Golden Delicious' but differs from 'Golden Delicious' in that it is resistant to apple scab, has freedom from stem cavity russet, bears a waxier skin, and green-tinged lenticels at harvest. This new variety of apple tree, now designated as COOP 16, was discovered by applicants in September, 1973, at Lafayette, Ind., in a cultivated area. The tree is a seedling of known parentage planted in 1966 in Block C of the Hinsley Breeding Orchard at the Horticultural Farm of the Purdue University Agricultural Experiment Station, West Lafayette, Ind. In the above orchard, its position was Row 21, Tree 79, having the description PRI 2174-3 in the breeding records. After observation, the selection was asexually propagated by grafting on seedling apple roots. The grafted material has maintained the described characteristics after propagation.

5 Drawing Figures

BACKGROUND OF THE INVENTION

Figure 1:
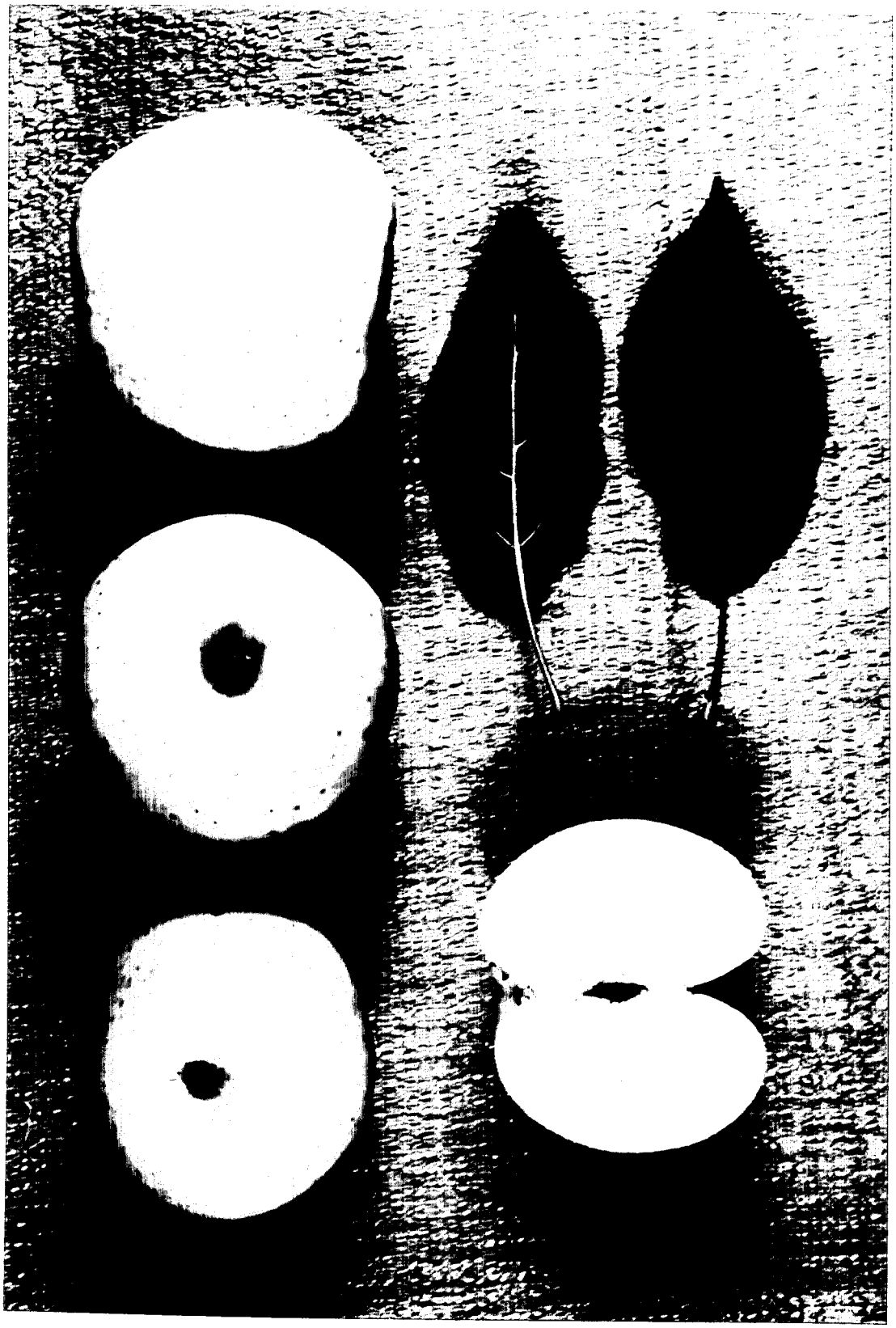
FIG. 1 is a photograph showing a typical example of fruit and foliage of COOP 16.

The present new cultivar is a seedling produced from crossing the seedling PRI 764-200 as the seed parent and the seedling PRI 672-100 as the pollen parent in 1965 at New Brunswick, N.J. This new cultivar carries the genetic factor $V_f$, inherited from *Malus floribunda* 821, which causes it to be resistant to infection caused by *Venturia inaequalis*. The presence of this genetic factor has been repeatedly proven by controlled greenhouse inoculation tests of the seedling and its offspring produced from controlled crosses. The complete pedigree is shown below:

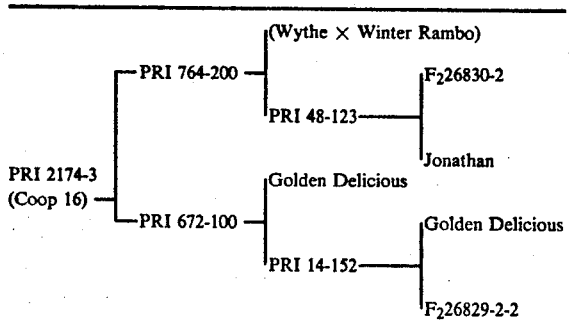

Both $F_2$26830-2 and $F_2$26829-2-2 have the following parentage:

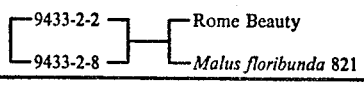

DETAILED DESCRIPTION OF THE NEW VARIETY

The following is a detailed description of this new cultivar with the color designation according to the Horticultural Colour Chart issued by the British Colour Council in collaboration with the Royal Horticultural Society.

Flower:

*Pedicel.*—2.0 cm (¾ inch) in length.

*Corolla.*—4.4 cm (1¾ inch) in diameter at anthesis.

*Color.*—Solferino purple from plate 26 in tight bud to 26/3 with open flowers.

Fruit:

*Shape.*—Conic to ovate.

*Size.*—Axial diameter 7.0 cm (2¾ inch).

*Color.*—Straw yellow (plate 604/1), occasional slight blush.

*Skin.*—Smooth, slightly waxy, conspicuous round rough dots resembling 'Golden Delicious' but green at harvest stage, medium thick and tough.

*Stem.*—2.5 cm (1 inch in length), medium thick.

*Cavity.*—Acute, deep, medium, smooth.

*Basin.*—Medium depth and breadth.

*Calyx.*—Persistent, convergent, partly closed.

*Calyx tube.*—Urn shaped.

*Stamens.*—Medium.

*Core line.*—Meeting.

*Core.*—Medium, closed, small.

*Carpels.*—Mucronate, elongated, tufted.

*Seed.*—Acute, non-tufted.

*Flesh.*—Texture: medium to coarse grained, granular, firm. Quality: very good, mild subacid, flavor resembles 'Golden Delicious'. Color: Empire yellow (plate 603/3).

*Maturity season.*—With 'Golden Delicious'.

*Keeping quality.*—Retains quality 5 months or more at 34° F.—fruit does not dehydrate after extended storage.

Tree:

*Tree.*—Moderately upright and vigorous.

*Leaves.*—Oval, single serrate margin, apex acuminate, base rounded, length to width ratio = 1.9.

What is claimed is:

1. A new and distinct apple tree as shown and described, resembling 'Golden Delicious', but particularly characterized by resistance to scab, waxy skin, good storage quality, maturity with 'Golden Delicious' approximately one week after 'Delicious' and four and one-half weeks after 'Prima'.

* * * * *